[19] United States Patent
Harrison et al.

[11] 4,260,765
[45] Apr. 7, 1981

[54] 2-(3-PYRIDYL)-5-THIAZOLECARBOXA-MIDES

[75] Inventors: William A. Harrison, Guelph, Canada; Winchester L. Hubbard, Woodbridge; Robert E. Grahame, Jr., Cheshire, both of Conn.

[73] Assignee: Uniroyal, Inc., New York, N.Y.

[21] Appl. No.: 45,809

[22] Filed: Jun. 5, 1979

Related U.S. Application Data

[63] Continuation of Ser. No. 861,768, Dec. 19, 1977, abandoned, which is a continuation-in-part of Ser. No. 140,571, May 5, 1971, abandoned.

[51] Int. Cl.$^3$ .......................................... C07D 417/04
[52] U.S. Cl. .................................... 546/280; 424/263; 546/193; 546/256; 546/270
[58] Field of Search ......................................... 546/280

[56] References Cited

U.S. PATENT DOCUMENTS 3,705,153  12/1972  Kaneko et al. .................. 546/280

Primary Examiner—Alan L. Rotman
Attorney, Agent, or Firm—Anthony Lagani, Jr.

[57] ABSTRACT

Certain 2-(3-pyridyl) thiazoles are useful for the control of insects, and are particularly effective against aphids. Many of these thiazoles are new compounds.

10 Claims, No Drawings

2-(3-PYRIDYL)-5-THIAZOLECARBOXAMIDES

This is a continuation, of application Ser. No. 861,768, filed Dec. 19, 1977 now abandoned which is a continuation-in-part of application Ser. No. 140,571 filed May 5, 1971 now abandoned and relates to the use of certain 2-(3-pyridyl) thiazoles for use in selectively controlling insects, and, particularly, aphids. Many of these thiazoles are new compounds.

Some 2-(3-pyridyl) thiazoles are known from the prior art. See, for example, the following references:

Karrer and Schukri, Helv. Chim. Acta 28, 820 (1945); Chemical Abstracts (CA) 54, 4571c (1960); C. A. 54, 9891c (1960); C. A. 55, 24739e (1961); C. A. 57, 16586b; C. A. 57, 9813b (1962); C. A. 49, 8249C (1955); C. A. 62, 10440g (1965); C. A. 62, 7764c (1965); C. A. 65, 8919b (1966); C. A. 48, 1341a (1954); C. A. 59, 11936b (1963); C. A. 63, 3496a (1965); and C. A. 59, 635de (1963).

However, none of these articles discloses such thiazoles as being useful in controlling insects.

In accordance with this invention, insects are effectively controlled using 2-(3-pyridyl) thiazoles or acid salts thereof, of the general formula (I):

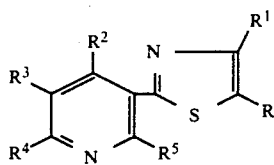

wherein: $R^2$, $R^3$, $R^4$ and $R^5$ can be the same or different and can be hydrogen or an alkyl group containing up to 3 carbon atoms, and R and $R^1$ can be the same or different and are:

(a) hydrogen
(b) an alkyl group containing up to 6 carbon atoms
(c) a cycloalkyl group containing 5 to 8 carbon atoms
(d) a cyano group
(e) a nitro group
(f) —$R^{10}COXR^6$ wherein $R^{10}$ is a single covalent bond or a divalent aliphatic acyclic hydrocarbyl group containing 1 to 3 carbon atoms, X is divalent sulfur or oxygen, and $R^6$ can be
  (i) hydrogen
  (ii) a metal ion selected from the group, consisting of aluminum, cadmium, calcium, cobalt, copper, iron, lithium, magnesium, manganese, mercury, nickel, potassium, sodium and, zinc, or a primary or secondary alkylammonium or alkanolammonium moiety
  (iii) an alkyl, alkenyl or alkynyl group containing up to 12 carbon atoms
  (iv) a cycloalkyl or cycloalkenyl group containing 5 to 8 carbon atoms
  (v) an aryl, aralkyl, alkyl substituted aralkyl, or alkaryl group containing 6 to 10 carbon atoms
  (vi) an hydroxyalkyl, alkoxyalkyl, alkylaminoalkyl, or aralkylaminoalkyl group containing up to 10 carbon atoms
(g) —$R^{10}COR^7$ where $R^{10}$ has the meaning specified in (f) and wherein $R^7$ can be:
  (i) hydrogen
  (ii) an alkyl group containing 1 to 3 carbon atoms or phenyl
  (iii) an —$NR^8R^9$ group wherein $R^8$ and $R^9$ can be the same or different and can be hydrogen, alkyl, alkenyl, alkynyl, hydroxyalkyl, alkoxyalkyl, aminoalkyl, and alkylaminoalkyl containing up to 8 carbon atoms, a cycloalkyl or cycloalkenyl of 5 to 8 carbon atoms, an aryl, haloaryl, aralkyl or alkaryl having 6 to 10 carbon atoms, or a nitrogen-containing hererocyclic aromatic radical having 5 to 10 carbon atoms, or $R^8$ and $R^9$ are joined together to form an alkyl substituted or non-substituted ring structure containing 4 to 7 carbon atoms and up to 2 atoms selected from nitrogen and oxygen, or $R^8$ or $R^9$ forms an alkylene group of 2 to 4 carbon atoms joining two members of the general formula, the members being the same or different.

(h) $R^1$ and R are joined together to form a benzene ring fused to the thiazole ring; or, an acid salt or metal complex of said general formula compound.

Acid salts and metal complexes of these thiazoles are also effective in controlling insects, particularly the salts made by reaction with hydrogen chloride, hydrogen bromide, hydrogen iodide, and sulfuric acid. The metal complexes can be of the types described in the book entitled *Pyridine and its Derivatives*, E. Klingsberg, editor, part I, pages 40 ff., Interscience Publishers, New York, 1960.

Within the generic class, the preferred compounds of the general formula (I) are those where: $R^2$, $R^3$, $R^4$ and $R^5$ can be hydrogen or methyl, R can be:
(a) hydrogen
(b) methyl
(c) a cyano group
(d) a nitro group
(e) —$R^{10}COXR^6$ wherein $R^{10}$ is a single covalent bond or methylene, X is divalent sulfur or oxygen, and $R^6$ can be:
  (i) hydrogen
  (ii) a metal salt selected from the group consisting of sodium, potassium and zinc, or a primary or secondary alkylammonium or alkanolammonium moiety
  (iii) an alkyl, alkenyl or alknyl group containing up to 5 carbon atoms
  (iv) a cycloalkyl group having 5 to 6 carbon atoms
  (v) phenyl
  (vi) an hydroxyalkyl, alkoxyalkyl, or alkylaminoalkyl group containing up to 4 carbon atoms
(f) —$R^{10}COR^7$ wherein $R^{10}$ has the meaning specified in (e) and wherein $R^7$ can be:
  (i) hydrogen
  (ii) methyl
  (iii) —$NR^8R^9$ wherein $R^8$ and $R^9$ can be the same or different and can be hydrogen, an alkyl, alkenyl, alkynyl, hydroxyalkyl or alkoxyalkyl having up to 4 carbon atoms, an aminoalkyl or alkylaminoalkyl having no more than 5 carbon atoms wherein the sum of the carbon atoms of $R^8$ and $R^9$ is no greater than 6, a cycloalkyl having 5 to 6 carbon atoms, phenyl, or $R^8$ and $R^9$ are joined together to form an alkyl substituted or non-substituted ring structure containing 4 to 6 carbon atoms and up to 2 atoms selected from nitrogen and oxygen $R^1$ can be:
(a) hydrogen
(b) an alkylyl having from 1 to 3 carbon atoms (c) —R$^{10}$COXR$^6$ wherein R$^{10}$ is methylene, X is divalent sulfur or oxygen, and R$^6$ can be hydrogen, an alkyl having 1 to 2 carbon atoms, or NH$_2$; or, an acid salt or metal complex of said general formula compound.

The most preferred compounds of the general formula (I) are those where: R$^2$, R$^3$, R$^4$ and R$^5$ are hydrogen, R can be hydrogen, methyl, ethyl, a cyano group, a nitro group or —COXR$^6$ wherein X, is divalent sulfur or oxygen and wherein R$^6$ can be:

(a) an alkyl, alkenyl, alkynyl, hydroxyalkyl, alkoxyalkyl, or alkylaminoalkyl group having up to 4 carbon atoms or (b) phenyl or cyclohexyl, or R is —CONR$^8$R$^9$ wherein R$^8$ and R$^9$ can be the same or different and can be hydrogen or alkyl group having 1 to 3 carbon atoms, or when either R$^8$ or R$^9$ is hydrogen, the other group can be an hydroxyalkyl having up to 2 carbon atoms, an alkoxyalkyl having 1 to 4 carbon atoms, alkylaminoalkyl having 1 to 5 carbon atoms or a cyclohexyl radical, or R$^8$ and R$^9$ can be joined together to form a ring structure which can contain an oxygen atom, and R$^1$ can be hydrogen, methyl, —CH$_2$COOCH$_3$, —CH$_2$COOC$_2$H$_5$, or —CH$_2$CONH$_2$; or, a salt complex formed by the association of said general formula compound with an acid selected from the group HCl, HBr, HI and H$_2$SO$_4$.

Compounds falling within the scope of general formula (I) and found useful in controlling insects include:
2-(3-pyridyl)-4-ethyl-5-propylthiazole
5-propyl-2-(3-pyridyl)thiazole
4-propyl-2-(3-pyridyl)-5-thiazolecarbonitrile
5-nitro-4-propyl-2-(3-pyridyl)thiazole, the HCl salt thereof
2-(3-pyridyl)-4-thiazolecarbonitrile
N,N-dimethyl-2-(3-pyridyl)-4-thiazolepropionamide
N,N,4-trimethyl-2-(3-pyridyl)-5-thiazoleacetamide
N,N,N',N'-tetramethyl-2-(3-pyridyl)-4,5-thiazole dicarboxamide
Dichloro [N,N,4-trimethyl-2-(3-pyridyl)-5-thiazolecarboxamide]zinc
N-butyl-N,4-dimethyl-2-(3-pyridyl)-5-thiazole carboxamide
2-(5-methyl-3-pyridyl)benzothiazole
N,N-diethyl-5-nitro-2-(3-pyridyl)-4-thiazoleacetamide It is of particular significance to note that the compounds of the invention derive their useful activity from the -2-(3-pyridyl)thiazole moiety whereas substituents R-R$^5$ are important only to the extent of controlling the degree of activity of the compounds.

The compounds of this invention are generally effective against insects of the class Insecta and particularly insects in the orders Hemiptera and Homoptera. In these orders, members of the families Aphididae (aphids), Psyllidae (psyllas) and Aleyrodidae (white flies) are controlled most effectively.

Table A below lists some of the harmful insects which these compounds control effectively.

TABLE A

| Order Homoptera | | |
|---|---|---|
| Common Name | Scientific Name | Common Name of Host Plant |
| Family Aphididae | | |
| Green apple aphid | *Aphis pomi* | Apple |
| Rosy apple aphid | *Auraphis rosea* | Apple |
| Apple grain aphid | *Rhopalosiphum prunifoliae* | Barley |

TABLE A-continued

| Order Homoptera | | |
|---|---|---|
| Common Name | Scientific Name | Common Name of Host Plant |
| Corn leaf aphid | *Rhopalosiphium maidis* | Barley |
| Green cabbage aphid | *Brevicoryne brassica* | Collard |
| Cotton aphid | *Aphis gossypii* | Cotton |
| Green peach aphid | *Myzus persicae* | Cotton |
| Black bean aphid | *Aphis fabae* | Cow peas |
| Black pecan aphid | *Timocallis caryaefoliae* | Pecan |
| Yellow aphid | *Monellia spp.* | Pecan |
| Pea aphid | *Macrosiphum pisi* | Broadbean |
| Family Psyllidae | | |
| Pear Psylla | *Psylla pyricola* | Pear |
| Family Aleyrodidae | | |
| Greenhouse white fly | *Trialeurodes vaporariorum* | Tobacco |

Beneficial insects, such as hymenopterous wasps, which feed upon aphids, are apparently unaffected by these compounds at dosage rates effective for aphid control. Other beneficial insects which enjoy similar advantages include lady bird beetles (Coccinellidae), syrphid fly larvae (Syrphidae) and lace wings (Chrysopidae), and parasitic insects of superfamilies such as Ichneumonidea and Chalcidoidea.

For practical applications, the compounds of the invention can be used alone, or dissolved or suspended in suitable carriers such as water, alcohols, ketones, phenols, toluene or xylenes. Optionally, one or more surface active agent and/or inert diluent can be added to the formulation to facilitate handling. The formulations can take the form of dusts, granules, wettable powders, emulsifiable concentrates, water solution concentrates, or a water soluble solid.

These formulations will contain amounts of the compounds effective for the particular method of insect control. These amounts can vary widely; typically, the range is from 0.1 to 95% active ingredient. Spray dilutions can contain from a few parts per million to full strength concentrates applied by ultra low volume techniques. Concentration per unit area, where plants are the area treated, can vary from 0.1 to 10 pounds per acre.

Commonly, the compounds are applied directly to the insects, or to areas the insects occupy. To control aphids, for example, sprays of the compounds are applied to the aphids directly, to plants upon which they feed, or both. Sprays applied to the aphid-infested plants kill effectively even if direct contact does not occur, as where the aphids cling to the inner surface of a curled up leaf or lie in a protected leaf sheath of, for example, a grain plant. Another effective method of attack involves application of the compounds to the soil or other medium in which insect-infested plants live. The compounds act systemically upon the insects after the compound is absorbed by the plants.

Harmful insects attack a wide variety of plants, including both ornamental and agricultural plants such as chrysanthemum, azalea, cotton, corn, wheat, apple and tobacco, and inflict damage by withdrawing vital juices from the plants, by secreting toxins, and often by transmitting diseases. These compounds can prevent such damage. The methods of application, and the selection and concentration of these compounds, will be varied depending upon such circumstances as area, climate, prevalent diseases, etc. One skilled in the art can select the proper approach by simple experiments.

Many of the insecticidal compounds of this invention are new. The new compounds have the general formula (I) and include those where $R^2$, $R^3$, $R^4$ and $R^5$ can be the same or different and can be hydrogen or an alkyl group containing up to 3 carbon atoms, and R and $R^1$ can be the same or different and are:

(a) hydrogen, provided $R^1$ is not hydrogen, methyl, —COOH or —COOC$_2$H$_5$
(b) methyl, provided $R^1$ is not hydrogen
(c) an alkyl group containing up to 6 carbon atoms
(d) a cycloalkyl group containing 5 to 8 carbon atoms
(e) a cyano group
(f) a nitro group
(g) —$R^{10}$COX$R^6$ wherein $R^{10}$ is a single covalent bond or a divalent aliphatic acyclic hydrocarbyl group containing 1 to 3 carbon atoms, X is divalent sulfur or oxygen, and $R^6$ can be
  (i) hydrogen
  (ii) a metal ion selected from the group consisting of aluminum, cadmium, calcium, cobalt, copper, iron, lithium, magnesium, manganese, mercury, nickel, potassium, sodium and zinc, or a primary or secondary alkylammonium or alkanolammonium moiety
  (iii) an alkyl, alkenyl or alkynyl group containing up to 12 carbon atoms
  (iv) a cycloalkyl or cycloalkenyl group containing 5 to 8 carbon atoms
  (v) an aryl, aralkyl, alkyl substituted aralkyl, or alkaryl group containing 6 to 10 carbon atoms
  (vi) an hydroxyalkyl, alkoxyalkyl, alkylaminoalkyl, or aralkylaminoalkyl group containing up to 10 carbon atoms.
(h) —$R^{10}$CO$R^7$ where $R^{10}$ has the meaning specified in (g) and wherein $R^7$ can be:
  (i) hydrogen
  (ii) an alkyl group containing 1 to 3 carbon atoms or phenyl
  (iii) an —NR$^8$R$^9$ group wherein $R^8$ and $R^9$ can be the same or different and can be: hydrogen, alkyl, alkenyl, alkynyl, hydroxyalkyl, alkoxyalkyl, aminoalkyl and alkylaminoalkyl containing up to 8 carbon atoms, a cycloalkyl or cycloalkenyl of 5 to 8 carbon atoms, an aryl, haloaryl, aralkyl, alkaryl having 6 to 10 carbon atoms, or nitrogen-containing heterocyclic aromatic radical having 5 to 10 carbon atoms, or $R^8$ and $R^9$ are joined together to form an alkyl substituted or non-substituted ring structure containing 4 to 7 carbon atoms and up to 2 atoms selected from nitrogen and oxygen, or $R^8$ or $R^9$ forms an alkylene group of 2 to 4 carbon atoms joining two members of the general formula, the members being the same or different; or, an acid salt or metal complex of said general formula compound.

A more preferred group of the new compounds are those where: $R^2$, $R^3$, $R^4$ and $R^5$ can be hydrogen or methyl, R can be:
(a) hydrogen or methyl, provided $R^1$ is not hydrogen, alkyl, —COOH, or —COOC$_2$H$_5$
(b) a cyano group
(c) a nitro group (d) —$R^{10}$COX$R^6$ wherein $R^{10}$ is a single covalent bond or methylene, X is divalent sulfur or oxygen and $R^6$ can be:
  (i) hydrogen
  (ii) a metal salt selected from the group consisting of sodium, potassium and zinc, or a primary or secondary alkylammonium or alkanolammonium moiety
  (iii) an alkyl, alkenyl or alkynyl group containing up to 5 carbon atoms
  (iv) a cycloalkyl group having 5 to 6 carbon atoms
  (v) phenyl
  (vi) an hydroxyalkyl, alkoxyalkyl, or alkylaminoalkyl group containing up to 4 carbon atoms
(e) —$R^{10}$CO$R^7$ wherein $R^{10}$ has the meaning specified in (d) and wherein $R^7$ can be:
  (i) hydrogen
  (ii) methyl
  (iii) —NR$^8$R$^9$ wherein $R^8$ and $R^9$ can be the same or different and can be hydrogen, an alkyl, alkenyl, alkynyl, hydroxyalkyl or alkoxyalkyl having up to 4 carbon atoms, an aminoalkyl or alkylaminoalkyl having no more than 5 carbon atoms wherein the sum of the carbon atoms of $R^8$ and $R^9$ is no greater than 6, a cycloalkyl having 5 to 6 carbon atoms, phenyl, or $R^8$ and $R^9$ are joined together to form an alkyl substituted or non-substituted ring structure containing 4 to 6 carbon atoms and up to 2 atoms selected from nitrogen and oxygen $R^1$ can be:
(a) hydrogen, provided R is not hydrogen or alkyl
(b) alkyl having from 1 to 3 carbon atoms, provided R is not hydrogen,
(c) —CH$_2$COX$R^6$ wherein X is divalent sulfur or oxygen, and $R^6$ can be hydrogen, an alkyl having 1 to 2 carbon atoms
(d) CH$_2$CONH$_2$; or, an acid salt or metal complex of said general formula compound.

The most preferred group of the new compounds are those where: $R^2$, $R^3$, $R^4$ and $R^5$ are hydrogen, R, when $R^1$ is methyl, can be methyl, ethyl, a cyano group, a nitro group or —COX$R^6$ wherein X is divalent sulfur or oxygen and wherein $R^6$ can be: an alkyl, alkenyl, alkynyl or alkylaminoalkyl group having up to 4 carbon atoms, cyclohexyl or phenyl, or R is —CONR$^8$R$^9$ or —CH$_2$CONR$^8$R$^9$ wherein $R^8$ and $R^9$ can be the same or different and can be hydrogen or an alkyl group having 1 to 3 carbon atoms, or when either $R^8$ or $R^9$ is hydrogen, the other group can be an hydroxyalkyl radical having up to 2 carbon atoms, an alkoxyalkyl having up to 4 carbon atoms, alkylaminoalkyl radical having up to 5 carbon atoms or cyclohexyl, or $R^8$ and $R^9$ can be joined together to form a ring structure having 4 to 5 carbon atoms and which can contain an oxygen atom $R^1$, can be methyl provided R is methyl, and can be —CH$_2$COOCH$_3$, —CH$_2$COOC$_2$H$_5$, —CH$_2$CONH$_2$ provided R is hydrogen; or, a salt complex formed by the association of said general formula compound with an acid selected from the group HCl, HBr, HI and H$_2$SO$_4$.

Examples of these new compounds are:
4-methyl-2-(3-pyridyl)5-thiazolecarboxamide
N,4-dimethyl-2-(3-pyridyl)-5-thiazolecarboxamide
N-ethyl-4-methyl-2-(3-pyridyl)-5-thiazolecarboxamide N-isopropyl-4-methyl-2-(3-pyridyl)-5-thiazolecarboxamide N-isobutyl-4-methyl-2-(3-pyridyl)-5-thiazolecarboxamide N-tert-butyl-4-methyl-2-(3-pyridyl)-5-thiazolecarboxamide N-(2-hydroxyethyl)-4-methyl-2-(3-pyridyl)-5-thiazolecarboxamide N-(3-dimethylaminopropyl)-2-(3-pyridyl)-4-methyl-5-thiazolecarboxamide N,N-4-trimethyl-2-(3-pyridyl)-5-thiazolecarboxamide N,N-diethyl-4-methyl-2-(3-pyridyl)-5-thiazolecarboxamide, and its sulfuric acid salt N,N-diisopropyl-4-methyl-2-(3-pyridyl)-5-thiazolecarboxamide 4-[4-methyl-2-(3-pyridyl)-5-thiazolylcarbonyl]morpholine N-dodecyl-4-methyl-2-(3-pyridyl)-5-thiazolecarboxylate and its hydrochloric acid salt 2-(3-pyridyl)-4-thiazolecarboxamide N-methyl-2-(3-pyridyl)-4-thaizolecarboxamide 4-[2-(3-pyridyl)-4-thiazolylcarbonyl]morpholine 4-methyl-5-nitro-2-(3-pyridyl)thiazole, and its hydrochloric acid salt.

The new compounds of this invention can be made by prior art processes, most conveniently by reacting the appropriate thioamide (II), such as thionicotinamide or a derivative of thionicotinamide, with an alpha halocarbonyl compound (III, where X' is chlorine or bromine). The resulting 2-(3-pyridyl)thiazole hydrohalide salt (IV) may be isolated as such or can be converted to the base (V). The synthesis can be represented by the following equation:

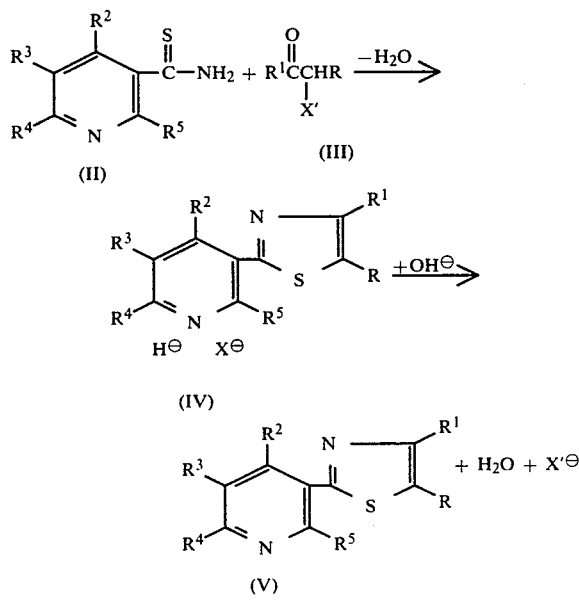

The synthesis can be performed by mixing the thionicotinamide, or alkyl-substituted thionicotinamide with an equivalent quantity of the halocarbonyl compound in a suitable polar solvent, such as methanol, ethanol, isopropyl alcohol, 2-methoxyethanol or dimethylformamide, and heating the mixture to about 60° to 100° C. for several hours (usually from two to ten hours). In general, yields are improved by slowly adding to the reactants an approximately equivalent amount, or slightly (preferably two-thirds to one equivalent) less of a tertiary amine such as triethylamine or other suitable organic base such as pyridine, during the course of the reaction. A weak inorganic base such as sodium bicarbonate can also be used.

The addition of the base probably assists the reaction by neutralizing hydrogen halide which otherwise would form a salt with the thionicotinamide and impede its reaction with the halocarbonyl compound. Without addition of base, reaction of equimolar quantities of thionicotinamide and ethyl 2-chloroacetoacetate, for example, gives ethyl 4-methyl-2-(3-pyridyl)-5-thiazolecarboxylate in yields of only 35–40% whereas when an equivalent amount of triethylamine is added, yields of 70–75% are obtained.

Alternatively, the halocarbonyl compound may be reacted with approximately two equivalents of thionicotinamide or thionicotinamide derivative and the unused thioamide recovered from its hydrogen halide salt. Thus, the synthesis, as usually performed in making the chemicals of this invention, can be represented as follows:

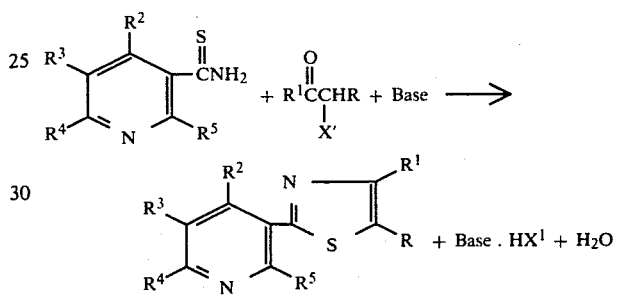

where B is excess thioamide or another organic base such as pyridine or triethylamine. (When sodium bicarbonate is used, carbon dioxide, water and sodium chloride are formed instead of Base .HX.) Yields can also be improved by removing the water formed as the reaction proceeds. The water can be conveniently removed by azeotropic distillation at atmospheric pressure or under reduced pressure, depending on the solvent or solvents used and the reaction temperature required. Solvents such as butanol, 4-methyl-2-pentanol, 2-methoxyethanol or mixtures of solvents such as butanol and benzene or toluene are suitable reaction media under these conditions. For example, N,N,4-trimethyl-2-(3-pyridyl)-5-thiazolecarboxamide is obtained in yields of 60–65% when 2-chloro-N,N-dimethylacetoacetamide is reacted with two equivalents of thionicotinamide in 1-butanol at 75° C. without water removel. However, if the water formed is removed by azeotropic distillation during the reaction, yields are improved to 70–75%.

Some of the chemicals prepared by the above methods, in particular in the lower alkyl esters of the carboxyl and carboxymethyl derivatives, such as ethyl 4-methyl-2-(3-pyridyl)-5-thiazolecarboxylate, methyl 2-(3-pyridyl)-5-thiazolecarboxylate or methyl 2-(3-pyridyl)-4-thiazoleacetate, may be employed as intermediates in making other chemicals of the invention. For example, ethyl 4-methyl-2-(3-pyridyl)-5-thiazolecarboxylate is readily hydrolyzed by heating with aqueous alkali (e.g., sodium hydroxide), and subsequent neutralization of the hydrolysis mixture with acid (e.g., hydrochloric acid or acetic acid) precipitates 4-methyl-2-(3-pyridyl)-5-thiazolecarboxylic acid.

Treatment of this acid with thionyl chloride in a suitable solvent, such as chloroform or toluene, yields 4-methyl-2-(3-pyridyl)-5-thiazolecarbonyl chloride hydrochloride which can be reacted with ammonia, or a primary or secondary amine, to obtain the corresponding amides. The acid chloride hydrochlorides can also be used as intermediates for making other derivatives, such as esters, and thioesters.

The following examples illustrate preparation of the compounds of the invention, and their effective, often selective, attack upon insects.

EXAMPLE I

Preparation of Ethyl 4-Methyl-2-(3-Pyridyl)-5-Thiazolecarboxylate

Thionicotinamide (207 g., 1.50 moles), isopropyl alcohol (600 ml.) and ethyl 2-chloroacetoacetate (250 g., 1.52 moles) were placed in a flask equipped with a condenser and heated with stirring to 85°–90° C. About one-half hour later, slow dropwise addition of triethylamine (158 g., 1.56 moles) was begun. The addition was made during a period of six hours, and no solid remained in the reaction mixture after about three-quarters of the amine had been added. The solution subsequently darkened considerably. Heating was continued for one hour after all the triethylamine had been added. When the reaction mixture was cooled, a crystalline precipitate formed, and was removed by filtration. The crystals (174 g.) were mainly triethylamine hydrochloride. The filtrate was evaporated under reduced pressure, and water (500 ml.) and toluene (750 ml.) added to the residue. After a small amount of insoluble material (mostly thionicotinamide) had been removed by filtration, the toluene and water layers were separated.

The toluene layer was washed three times with ice-cold aqueous 5% sodium hydroxide (total volume: 600 ml.), and once with water (200 ml.), and was then extracted three times with dilute hydrochloric acid (total volume: 1200 ml., prepared by diluting 200 ml. of concentrated, i.e., 37%, acid). When the combined acid extracts were cooled in ice and made basic with aqueous ammonia, an oily precipitate was obtained which solidified within a few minutes. The solid was broken up, filtered off, washed with water and dried. The light tan product (267 g., 72% yield) melted at 55°–58° C.

Petroleum ether or aqueous ethanol are suitable solvents for recrystallization. An analytical sample, melting point (m.p.) 57°–60° C., recrystallized from ethanol-water, was found to contain 57.95% carbon, 4.86% hydrogen and 11.06% nitrogen. The values calculated for $C_{12}H_{12}N_2O_2S$ are 58.04%, 4.87%, and 11.28%, respectively. The melting point of the chemical varied slightly from batch to batch, but in general melting occurred over a range of three to five degrees between 55° and 62° C. (because the product exists in two crystalline forms, one melting at about 58°, and the other, at 62° C.)

EXAMPLE II

Preparation of 4-Methyl-2-(3-Pyridyl)-5-Thiazolecarboxylic Acid

A solution of sodium hydroxide (22 g. 0.55 mole) in water (300 ml.) was mixed with a solution of ethyl 4-methyl-2-(3-pyridyl)-5-thiazolecarboxylate (124 g., 0.50 mole) in 95% ethanol (150 ml.). The mixture was heated and stirred for about ten minutes on a steam bath, and then allowed to stand for one hour without further heating. When the ice-cooled reaction mixture was neutralized with dilute hydrochloric acid and acidified with acetic acid, a thick precipitate of finely divided white solid was obtained. The solid was collected by filtration, washed thoroughly with water, and dried in an oven at 110° C. The product (106 g., 96% yield) melted with decomposition at 249°–250° C.

EXAMPLE III

Preparation of N,N-Diethyl-4-Methyl-2-(3-Pyridyl)-5-Thiazolecarboxamide and its Sulfate A solution of thionyl chloride (40 g., 0.34 mole) in toluene (50 ml.) was added dropwise over a time period of one-half hour to a stirred suspension of powdered 4-methyl-2-(3-pyridyl)-5-thiazolecarboxylic acid (44 g., 0.20 mole) in toluene (450 ml.) at 50° C. The stirred reaction mixture, which became quite viscous during the addition, was maintained at 50°–60° C. for another three hours. The heat was removed and a stream of dry air was bubbled slowly through the mixture for about one hour while it cooled.

The mixture as cooled further in an ice bath and then filtered to remove the solid, crude 4-methyl-2-(3-pyridyl)-5-thiazolecarboxylic acid chloride hydrochloride, which was washed with fresh toluene (100 ml.) and partially air-dried. The solid was transferred in portions over one-half hour to a stirred, ice-cooled solution of diethylamine (60 g.) in toluene (400 ml.). After the addition was completed the ice-bath was removed, and the reaction mixture left overnight at room temperature. The toluene solution was then washed three times with water (50 ml. each time), dried over anhydrous sodium sulfate, filtered and evaporated under reduced pressure on a steam bath.

Elemental analysis and the nuclear magnetic resonance spectrum of the residual viscous amber liquid (49 g., 89% yield) confirmed that, apart from a remaining trace of toluene, the product was almost pure N,N-diethyl-4-methyl-2-(3-pyridyl)-5-thiazolecarboxamide. After storage in a freezer for several weeks at −15° C., the product crystallized, m.p. 39°–41° C.

Treatment of a cold solution of the amide (14 g.) in ethyl acetate (75 ml.) with a cold solution of sulfuric acid (5 g.) in absolute ethanol (20 ml.) gave an immediate precipitate (15.2 g.) of the sulfate salt, m.p. 148°–150° C. Analytical results (C, 45.00%; H, 5.03%) were in agreement with the formula $C_{14}H_{19}N_3O_5S_2$, indicating combination of amide and sulfuric acid.

EXAMPLE IV

Preparation of N,N,4-Trimethyl-2-(3-Pyridyl)-5-Thiazolecarboxamide

Crude 2-chloro-N,N-dimethylacetoacetamide (40 g., about 10% of which was 2,2-dichloro-N,N-dimethylacetoacetamide), prepared by reacting N,N-dimethylacetoacetamide with sulfuryl chloride in toluene at approximately 0° C., was mixed with thionicotinamide (55.2 g., 0.4 mole) and 1-butanol (250 ml.) in a reaction flask equipped with a stirrer, thermometer, Dean-Stark trap and condenser. The mixture was heated with stirring and the pressure in the apparatus lowered until boiling took place at 75° C. and the butanol-water azeotrope slowly distilled into the Dean-Stark trap. A total of 11 ml. of distillate, the aqueous layer of which was slightly over 3 ml., was collected during the next four hours. The rest of the butanol was then evaporated under vacuum at a maximum temperature of 80° C. The residue was treated with toluene (350 ml.) and the undissolved solid (A) collected by filtration. The filtrate was washed three times with a total of 100 ml. of 15% aqueous sodium hyroxide solution and extracted with dilute hydrochloric acid (30 ml. of 37% acid diluted to 120 ml.). The acid extract was made basic with aqueous ammonia and extracted with 150, 50 and 50 ml. portions of chloroform. The combined chloroform extracts were dried with anhydrous sodium sulfate, filtered and evaporated. The viscous amber liquid residue crystallized on cooling. Yield of N,N,4-trimethyl-2-(3-pyridyl)-5-thiazolecarboxamide: 38.3 g. m.p. 62°-67° C. Recrystallization from ethyl acetate-hexane or toluene-ligroin raised the melting point to 67°-68° C.

Most of solid A (36.5 g.) dissolved when treated with 300 ml. of water and 5 ml. of concentrated hydrochloric acid. Basification of the filtered solution with aqueous ammonia precipitated thionicotinamide (25.7 g., m.p. 183°-185° C. decomp.). The yield of N,N,4-trimethyl-2-(3-pyridyl)-5-thiazolecarboxamide based on thionicotinamide consumed in the reaction, was 72.5%. When the reaction was carried out at the same temperature without removal of water by azeotropic distillation the yield was decreased by about 10%. Recrystallization from toluene or toluene-ligroin also yielded another crystalline form of the product which melted at 93°-95° C. On storage, the lower melting form changed slowly to the higher melting form.

EXAMPLE V

Preparation of 4-Methyl-5-Nitro-2-(3-Pyridyl)Thiazole (or 3-(4-Methyl-5-Nitro-2-Thiazolyl)Pyridine) and its Hydrochloride 3-(4-Methyl-2-thiazolyl)pyridine hydrochloride (21.3 g.), prepared by the procedure of Karrer and Schukri [Helv. Chim. Acta 28, 820 (1945); Chem. Abstr. 40, 1502 (1946)], was added in portions to a cold mixture of concentrated sulfuric acid (50 ml.) and fuming nitric acid (40 ml.). The reaction mixture was warmed to 60°-65° C. for three hours and then heated on a steam bath for eight hours. The mixture was cooled, poured onto ice (300 g.), neutralized with cold 10% sodium hydroxide, and the product extracted with chloroform. Evaporation of the chloroform solution gave 17.5 g. (79% yield) of crude 4-methyl-5-nitro-2-(3-pyridyl)-thiazole, m.p. 106°-113° C. After recrystallization from ethanol the product melted at 113°-115° C.

Treatment of a filtered solution of the crude product (10 g.) in acetone with cold concentrated hydrochloric acid (4.5 ml.) gave an immediate precipitate (10.5 g., 90% yield) of the hydrochloride, m.p. product 197°-198° C. decomp. (dependent on rate of heating). Calculated from $C_9H_8ClN_3O_2S$: C, 41.94%; H, 3.13%. Found: C, 42.23% H, 3.13%.

The following Table B summarizes the preparation of the compound described therein. The preparation methods denoted by the letters A through F are:

A. Made directly by reaction of the appropriate thioamide and halocarbonyl compounds.
B. Made by alkaline hydrolysis of the corresponding methyl or ethyl ester.
C. Made from the corresponding pyridylthiazolecarboxylic or pyridylthiazoleacetic acid by way of the acid chloride hydrochloride.
D. Made by dehydration of the amide (see compound 17) with phosphorus pentoxide.
E. Made by nitration of the appropriate 3-(4-ethyl-2-thiazolyl)pyridine or its hydrochloride (Example V).
F. Made by ammonolysia of the corresponding methyl or ethyl ester.

The percent yields listed in Table B are based on the starting materials for the method indicated. For example, in the cases where method C is indicated, the yields given are for conversion of the appropriate pyridylthiazolecarboxylic or pyridylthiazoleacetic acid to the products named. The figures given do not represent optimum yields, and in many cases higher yields are possible.

TABLE B

| Compound No. | Name | R | $R^1$ | Method of Preparation | yield % | M.P. (°C.) | Salts Prepared | M.P. of Salt(°C.) |
|---|---|---|---|---|---|---|---|---|
| 1 | Methyl 4-methyl-2-(3-pyridyl)-5-thiazolecarboxylate | $COOCH_3$ | $CH_3$ | A | 71 | 105-107 | Hydrochloride | ca212d |
| 2 | Ethyl 4-methyl-2-(3-pyridyl)-5-thiazolecarboxylate | $COOC_2H_5$ | $CH_3$ | A | 72 | 56-58 60-62 | Hydrochloride Sulfate | 206-208d 205-208d |
| 3 | 4-Methyl-2-(3-pyridyl)-5-thiazolecarboxylic acid | COOH | $CH_3$ | B | 96 | 249-250d | Potassium | ca335d |
| 4 | Propyl 4-methyl-2-(3-pyridyl)-5-thiazolecarboxylate | $COO(CH_2)_2CH_3$ | $CH_3$ | A | 14 | 60-61 | | |
| 5 | Isopropyl 4-methyl-2-(3-pyridyl)-5-thiazolecarboxylate | $COOCH(CH_3)_2$ | $CH_3$ | A | 19 | 89-92 | Hydrochloride Sulfate | 205.5-207d 181-183 |
| 6 | Pentyl 4-methyl-2-(3-pyridyl)-5-thiazolecarboxylate | $COO(CH_2)_4CH_3$ | $CH_3$ | A | 64 | 35-36 | | |
| 7 | Dodecyl 5-thiazolecarboxylate | $COO(CH_2)_{11}CH_3$ | $CH_3$ | A | 5 | 39-42 | Hydrochloride | ca150 |
| 8 | Cyclohexyl 4-methyl-2-(3-pyridyl)-5-thiazolecarboxylate | $COOC_6H_{11}$ | $CH_3$ | A | 15 | 63-64 | | |
| 9 | Allyl 4-methyl 2-(3-pyridyl)-5-thiazolecarboxylate | $COOCH_2CH=CH_2$ | $CH_3$ | C | 29 | 83-85 | | |
| 10 | Propargy 4-methyl-2-(3-pyridyl)-5-thiazolecarboxylate | $COOCH_2C\equiv CH$ | $CH_3$ | C | 29 | 124-125 | | |
| 11 | Benzyl 4-methyl-2-(3-pyridyl)-5-thiazolecarboxylate | $COOCH_2C_6H_5$ | $CH_3$ | A | 20 | 83-85 | | |
| 12 | Phenyl 4-methyl-2-(3-pyridyl)-5-thiazolecarboxylate | $COOC_6H_5$ | $CH_3$ | C | 34 | 72-74 | | |
| 13 | Methoxyethyl 4-methyl-2-(3- | | | | | | | |

TABLE B-continued

| Compound No. | Name | R | $R^1$ | Method of Preparation | yield % | M.P. (°C.) | Salts Prepared | M.P. of Salt(°C.) |
|---|---|---|---|---|---|---|---|---|
|  | pyridyl)-5-thiazolecarboxylate | COOCH$_2$CH$_2$OCH$_3$ | CH$_3$ | A | 70 | 76–78 |  |  |
| 14 | Dimethylaminoethyl 4-methyl-2-(3-pyridyl)-5-thiazolecarboxylate | COOCH$_2$CH$_2$N(CH$_3$)$_2$ | CH$_3$ | C | 52 | 50–53 |  |  |
| 15 | Phenyl 4-methyl-2-(3-pyridyl)-5-thiazolecarbothiolate | COSC$_6$H$_5$ | CH$_3$ | C | 55 | 102–104 |  |  |
| 16 | 4-Methyl-2-(3-pyridyl)-5-thiazolecarboxamide | CONH$_2$ | CH$_3$ | C,F | 77 | 204–207 | Hydrochloride | 241–242d |
| 17 | 4-Methyl-2-(3-pyridyl)-5-cyanothiazole | C≡N | CH$_3$ | D | 40 | 98–100 |  |  |
| 18 | N,4-Dimethyl-2-(3-pyridyl)-5-thiazolecarboxamide | CONHCH$_3$ | CH$_3$ | C | 49 | 148–150 160–162 |  |  |
| 19 | N-Ethyl-4-methyl-2-(3-pyridyl)-5-thiazolecarboxamide | CONHC$_2$H$_5$ | CH$_3$ | C | 63 | 116–118 |  |  |
| 20 | 4-Methyl-N-propyl-2-(3-pyridyl)-5-thiaxolecarboxamide | CONH(CH$_2$)$_2$CH$_3$ | CH$_3$ | C | 52 | 109–110 |  |  |
| 21 | N-Isopropyl-4-methyl-2-(3-pyridyl)-5-thiazolecarboxamide | CONHCH(CH$_3$)$_2$ | CH$_3$ | C | 37 | 143–144 |  |  |
| 22 | N-Butyl-4-methyl-2-(3-pyridyl)-5-thiazolecarboxamide | CONH(CH$_2$)$_3$CH$_3$ | CH$_3$ | C | 43 | 95–97 |  |  |
| 23 | N-tert-Butyl-4-methyl-2-(3-pyridyl)-5-thiazolecarboxamide | CONHC(CH$_3$)$_3$ | CH$_3$ | C | 25 | 103–105 and 121–123 |  |  |
| 24 | N-Hexyl-4-methyl-2-(3-pyridyl)-5-thiazolecarboxamide | CONH(CH$_2$)$_5$CH$_3$ | CH$_3$ | C | 74 | 103–106 | Hydrochloride | 199–203d |
| 25 | 4-Methyl-N-octyl-2-(3-pyridyl)-5-thiazolecarboxamide | CONH(CH$_2$)$_7$CH$_3$ | CH$_3$ | C |  | 90–92 |  |  |
| 26 | 4-Methyl-N-tert-octyl-2-(3-pyridyl)-5-thiazolecarboxamide | CONHC(CH$_3$)$_2$CH$_2$C(CH$_3$)$_3$ | CH$_3$ | C |  | 85–87 |  |  |
| 27 | N-Cyclohexyl-4-methyl-2-(3-pyridyl)-5-thiazolecarboxamide | CONHC$_6$H$_{11}$ | CH$_3$ | C | 69 | 63–64 |  |  |
| 28 | N-Benzyl-4-methyl-2-(3-pyridyl)-5-thiazolecarboxamide | CONHCH$_2$C$_6$H$_5$ | CH$_3$ | C | 45 | 128–129 |  |  |
| 29 | 4-Methyl-2-(3-pyridyl)-5-thiazolecarboxamide | CONHC$_6$H$_5$ | CH$_3$ | A | 66 | 149–152 |  |  |
| 30 | N,N,4-Trimethyl-2-(3-pyridyl)-5-thiazolecarboxamide | CON(CH$_3$)$_2$ | CH$_3$ | A,C | 72,70 | 67–68; 93–95 |  |  |
| 31 | N,N-Diethyl-4-methyl-2-(3-pyridyl)-5-thiazolecarboxamide | CON(C$_2$H$_5$)$_2$ | CH$_3$ | A,C | 57,89 | 39–41 | sulfate | 148–150 |
| 32 | N,N-Diisopropyl-4-methyl-2-(3-pyridyl)-5-thiazolecarboxamide | CON[CH(CH$_3$)$_2$]$_2$ | CH$_3$ | C | 61 | 69–70 |  |  |
| 33 | N,N-Diisobutyl-4-methyl-2-(3-pyridyl)-5-thiazolecarboxamide | CON[CH$_2$CH(CH$_3$)$_2$]$_2$ | CH$_3$ | C | 23 | 71–72 |  |  |
| 34 | 1-[4-Methyl-2-(3-pyridyl)-5-thiazolecarbonyl] pyrrolidine |  | CH$_3$ | C | 66 | 75–77 |  |  |
| 35 | 1-[4-Methyl-2-(3-pyridyl)-5-thiazolecarbonyl] piperidine |  | CH$_3$ | C | 54 | 69–70 |  |  |
| 36 | 4-[4-Methyl-2-(3-pyridyl)-5-thiazolecarbonyl] morpholine |  | CH$_3$ | C | 69 | 121–123 |  |  |
| 37 | N-(2-Hydroxyethyl)-4-methyl-2-(3-pyridyl)-5-thiazolecarboxamide | CONHCH$_2$CH$_2$OH | CH$_3$ | C | 49 | 148–150 |  |  |
| 38 | N-(2-Aminoethyl)-4-methyl-2-(3-pyridyl)-5-thiazolecarboxamide | CONHCH$_2$CH$_2$NH$_2$ | CH$_3$ | C | 27 | 84–87 |  |  |
| 39 | N,N'-Ethylenebis-[4-methyl-2-(3-pyridyl)-5-thiazolecarboxamide] | CONHCH$_2$— | CH$_3$ | C | 55 | 287–292d |  |  |
| 40 | Ethyl 4-propyl-2-(3-pyridyl)-5-thiazolecarboxylate | COOC$_2$H$_5$ | (CH$_2$)$_2$CH$_3$ | A | 44 | 66–68 |  |  |
| 41 | 5-Acetyl-4-methyl-2-(3-pyridyl)thiazole | COCH$_3$ | CH$_3$ | A |  | 78–81 | Hydrochloride |  |
| 42 | 2-(3-Pyridyl)-4-thiazolecarboxamide | H | CONH$_2$ | C |  | 152–154 |  |  |
| 43 | N-Methyl-2-(3-pyridyl)-4-thiazolecarboxamide | H | CONHCH$_3$ | C | 65 | 113–115 |  |  |

TABLE B-continued

| Compound No. | Name | R | R¹ | Method of Preparation | yield % | M.P. (°C.) | Salts Prepared | M.P. of Salt(°C.) |
|---|---|---|---|---|---|---|---|---|
| 44 | N,N-Diethyl-2-(3-pyridyl)-4-thiazolecarboxamide | H | CON($C_2H_5$)$_2$ | C | | 64-66 | | |
| 45 | 4-[2-(3-Pyridyl)-4-thiazole-carbonyl]morpholine | H |  | C | | 134-136 | | |
| 46 | Methyl 2-(3-pyridyl)-4-thiazoleacetate | H | $CH_2COOCH_3$ | A | 21 | 64-66 | | |
| 47 | Ethyl 2-(3-pyridyl)-4-thiazoleacetate | H | $CH_2COOC_2H_5$ | A | 23 | 33-34 | Hydrochloride | |
| 48 | 2-(3-Pyridyl)-4-thiazoleacetic acid | H | $CH_2COOH$ | B | 86 | 192-194 | | |
| 49 | Ethyl 4-methyl-2-(5-methyl-3-pyridyl)-5-thiazolecarboxylate | $COOC_2H_5$ | $CH_3$ | A | 66 | 77-79 | | |
| 50 | Ethyl 4-methyl-2-(4-methyl-3-pyridyl)-5-thiazolecarboxylate | $COOC_2H_5$ | $CH_3$ | A | 35 | 60-63 | Hydrochloride | 195-197 |
| 51 | N-Isobutyl-4-methyl-2-(3-pyridyl)-5-thiazolecarboxamide | $CONHCH_2CH(CH_3)_2$ | $CH_3$ | C | 62 | 111-112 | | |
| 52 | N-sec-Butyl-4-methyl-2-(3-pyridyl)-5-thiazolecarboxamide | $CONHCH(CH_3)CH_2CH_3$ | $CH_3$ | C | 66 | 144-145 | | |
| 53 | 4-Methyl-N-(2-pyridyl)-2-(3-pyridyl)-5-thiazolecarboxamide |  | $CH_3$ | C | 41 | 184-186 | | |
| 54 | 4-Methyl-N-(3-dimethylaminopropyl)-2-(3-pyridyl)-5-thiazolecarboxamide | $CONH(CH_2)_3N(CH_3)_2$ | $CH_3$ | C | 43 | 54-56 | | |
| 55 | N,N-Diallyl-4-methyl-2-(3-pyridyl)-5-thiazolecarboxamide | $CON(CH_2CH=CH_2)_2$ | $CH_3$ | C | 61 | oil | | Calculated for $C_{16}H_{17}N_3OS$: C,64.18; H,5.72; N,14.04 Found: C, 64.17; H, 5.65; N, 14.11. |
| 56 | N,4-Dimethyl-2-(3-pyridyl)-5-thiazolecarboxanilide | $CON(CH_3)C_6H_5$ | $CH_3$ | C | 42 | 135-136 | | |
| 57 | N-Ethyl-4-methyl-2-(3-pyridyl)-5-thiazolecarboxanilide | $CON(C_2H_5)C_6H_5$ | $CH_3$ | C | 31 | 85-86 | | |
| 58 | N-(2-Hydroxyethyl)-N,4-dimethyl-2-(3-pyridyl)-5-thiazolecarboxamide | $CON(CH_3)CH_2CH_2OH$ | $CH_3$ | C | 68 | 83-84 | | |
| 59 | 2,6-Dimethyl-4-[4-methyl-2-(3-pyridyl)-5-thiazole-carbonyl]morpholine | 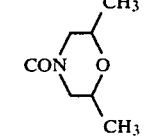 | $CH_3$ | C | 55 | Oil | | Calculated for $C_{16}H_{19}N_3O_2S$: C,60.54; H,6.03; N,13.24; Found: C,60.67; H,6.38; N,13.27 |
| 60 | Ethyl 4-methyl-2-(3-pyridyl)-5-thiazolecarbothiolate | $COSC_2H_5$ | $CH_3$ | C | 47 | 66-67 | | |
| 61 | 4-Ethyl-5-methyl-2-(3-pyridyl)-thiazole (or: 3-(4-ethyl-5-methyl-2-thiazolyl)-pyridine) | $CH_3$ | $C_2H_5$ | A | 40 | 45-47 | | |
| 62 | Methyl-5-methoxycarbonyl-2-(3-pyridyl)-4-thiazoleacetate | $COOCH_3$ | $CH_2COOCH_3$ | A | 34 | 84-86 | | |
| 63 | N-(3-Methoxypropyl)-4-methyl-2-(3-pyridyl)-5-thiazolecarboxamide | $CONH(CH_2)_3OCH_3$ | $CH_3$ | C | 55 | 85-86 | | |
| 64 | Diethyl 2-(3-pyridyl)-4,5-thiazoledicarboxylate | $COOC_2H_5$ | $COOC_2H_5$ | A | 11 | 69-71 | | |
| 65 | 4,5-Dimethyl-2-(3-pyridyl)thiazole (or: 3-(4,5-dimethyl-2-thiazolyl)-pyridine) | $CH_3$ | $CH_3$ | A | 33 | 63-65 | Hydrochloride | 194-196d |
| 66 | 4-Ethyl-2-(3-pyridyl)thiazole | | | | | | | |

TABLE B-continued

| Compound No. | Name | R | R¹ | Method of Preparation | yield % | M.P. (°C.) | Salts Prepared | M.P. of Salt(°C.) |
|---|---|---|---|---|---|---|---|---|
| | (or: 3-(4-ethyl-2-thiazolyl) pyridine) | H | $C_2H_5$ | A | 37 | 33-35 | Hydrochloride | 166-168 |
| 67 | Ethyl 5-methyl-2-(3-pyridyl)-4-thiazolecarboxylate | $CH_3$ | $COOC_2H_5$ | A | 31 | 48-51 | | |
| 68 | 4-Methyl-5-nitro-2-(3-pyridyl)-thiazole (or: 3-(4-methyl-5-nitro-2-thiazolyl)pyridine) | $NO_2$ | $CH_3$ | E | 79 | 113-115 | Hydrochloride | 197-198d |
| *69 | 4-Methyl-2-(3-pyridyl)thiazole (or: 3-(4-methyl-2-thiazolyl) pyridine) | H | $CH_3$ | A | 47 | 46-48 | Hydrochloride | 199-201 |
| *70 | Ethyl 2-(3-pyridyl)-4-thiazolecarboxylate | H | $COOC_2H_5$ | A | | 70-72 | Hydrobromide | |
| *71 | 2-(3-Pyridyl)-4-thiazolecarboxylic acid | H | COOH | B | 91 | 266-267d | | |
| 72 | 4-Chloro-4-methyl-2-(3-pyridyl)-5-thiazolecarboxanilide | $CONHC_6H_4$—p-Cl | $CH_3$ | A | 24 | 161-163 | | |
| 73 | 2-(3-pyridyl)-4,5-thiazoledicarboxy-o-toluidide | $CONHC_6H_4$—o-$CH_3$ | $CONHC_6H_4$—o-$CH_3$ | C | | 183-187 | | |
| 74 | 4-Ethyl-5-nitro-2-(3-pyridyl) thiazole | $NO_2$ | $CH_2CH_3$ | E | 60 | 82-84 | Hydrochloride | 173-176d |
| 75 | 4-Methyl-2-(3-pyridyl)-5-thiazole acetic acid ethyl ester | $\underset{CH_2C-OCH_2H_3}{\overset{O}{\parallel}}$ | $CH_3$ | A | 61 | 41.5-43.5 57-60 | | |
| 76 | 4-Methyl-2-(3-pyridyl)-5-thiazole acetic acid. | $\underset{CH_2C-OH}{\overset{O}{\parallel}}$ | $CH_3$ | B | 95 | 183-185 | | |
| 77 | 4-Methyl-3-(3-pyridly)-5-thiazoylyl phenyl ketone | $\overset{O}{\underset{C-\phantom{X}}{\parallel}}$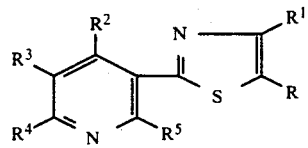 | $CH_3$ | A | 16 | 88-89 | | |
| 78 | 4-Methyl-2-(3-pyridyl)-5-thiazoleacetamide | $\underset{CH_2C-NH_2}{\overset{O}{\parallel}}$ | $CH_3$ | F | 57 | 213-215 | | |
| 79 | N,N,4-Trimethyl-2-(3-pyridyl)-5-thiazoleacetamide | $\underset{CH_2CN(CH_3)_2}{\overset{O}{\parallel}}$ | $CH_3$ | A | 17 | 77-79 | | |

In compounds 1 to 48, $R^2$, $R^3$, $R^4$, and $R^5$ are hydrogen.
In compound 49, $R^3$ is $CH_3$; in compound 50, $R^2$ is $CH_3$.
Compounds marked with an asterisk are not new.

The following examples illustrate the aphicidal use of the compounds of the invention.

EXAMPLE VI

The effectiveness of these compounds in controlling aphids was demonstrated by applying dilute sprays to barley seedlings infested with Corn Leaf Aphids, *Rhopalosiphum maidis,* and with the Apple Grain Aphid, *Rhopalosiphum prunifoliae.*

Compounds tested were prepared for spraying at 2000 ppm (parts per million) by dissolving the chemical in a small amount of acetone and adding a small amount of a suitable wetting agent. Typically, 0.5 gram of chemical was dissolved in 10 ml. acetone, two drops of Triton X100 wetting agent (octylphenoxy polyethoxy ethanol with 9-10 mole percent of polyethylene oxide) were added and this was dissolved or suspended in 250 milliliters (ml.) of water. Water soluble hydrochloride or sulfate salts were prepared by the addition of a wetting agent to the chemical with the proper amount of water, omitting the acetone solvent.

Barley seedlings, ten per cup, were grown for ten days in 12-ounce cups of soil. The seedlings were infested with corn leaf and apple grain aphids, and, two days later, the plants were sprayed thoroughly with the compound to be tested, covering all exposed foliage.

Five days later, results were found by determining the percent control of aphid populations on treated plants as compared to the population on untreated plants used as controls. Table C shows the percent control of aphids obtained at the spray concentration indicated.

TABLE C

Basic structure:

| Compound No. | R | R¹ | % Aphid Control (At p.p.m. Concentration) | Remarks |
|---|---|---|---|---|
| 1(69) | H | $CH_3$ | 99(500) | |
| 2 | H | $CH_3$ | 97(1000) | HCl salt of (1) |
| 3 | H | $C_2H_5$ | 97(500) | |

TABLE C-continued

Basic structure:

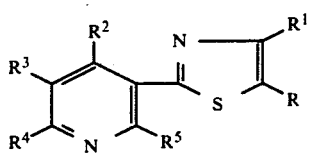

| No. | R³ | R | Yield % (mg/kg) | Notes |
|---|---|---|---|---|
| 4 | CH₃ | CH₃ | 96(1000) | |
| 5(65) | CH₃ | CH₃ | 93(500) | HCl salt of (4) |
| 6(61) | CH₃ | C₂H₅ | 60(1000) | |
| 7(67) | CH₃ | COOC₂H₅ | 40(1000) | |
| 8(17) | CN | CH₃ | 95(1000) | |
| 9 | NO₂ | CH₃ | 88(1000) | |
| 10(68) | NO₂ | CH₃ | 86(500) | HCl salt of (9) |
| 11(41) | COCH₃ | CH₃ | 93(2000) | |
| 12(3) | COOH | CH₃ | 93(2000) | |
| 13 | COOH | CH₃ | 77(2000) | |
| 14(1) | COOCH₃ | CH₃ | 97(2000) | |
| 15 | COOCH₃ | CH₃ | 93(500) | HCl salt of (14) |
| 16(2) | COOC₂H₅ | CH₃ | 100(1000) | |
| 17 | COOC₂H₅ | CH₃ | 100(2000) | HCl salt of (16) |
| 18 | COOC₂H₅ | CH₃ | 93(500) | SO₄ salt of (16) |
| 19(4) | COOC₃H₇ | CH₃ | 85(500) | |
| 20(5) | COO—i-C₃H₇ | CH₃ | 100(500) | |
| 21 | COO—i-C₃H₇ | CH₃ | 100(500) | HCl salt of (20) |
| 22(6) | COO—n-C₅H₁₁ | CH₃ | 90(1000) | |
| 23(7) | COO—n-C₁₂H₂₅ | CH₃ | 40(2000) | |
| 24(9) | COOCH₂CH=CH₂ | CH₃ | 90(500) | |
| 25(10) | COOCH₂C≡CH | CH₃ | 100(500) | |
| 26(8) | 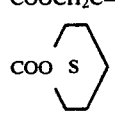 | CH₃ | 90(500) | |
| 27(12) | 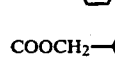 | CH₃ | 85(500) | |
| 28(11) | COOCH₂—⌬ | CH₃ | 80(2000) | |
| 29(13) | COO(CH₂)₂OCH₃ | CH₃ | 96(1000) | |
| 30(14) | COO(CH₂)₂N(CH₃)₂ | CH₃ | 80(500) | |
| 31(40) | COOC₂H₅ | n-C₃H₇ | 80(1000) | |
| 32(64) | COOC₂H₅ | COOC₂H₅ | 91(1000) | |
| 33(60) | COSC₂H₅ | CH₃ | 90(1000) | |
| 34(15) | COS—⌬ | CH₃ | 80(500) | |
| 35(16) | CONH₂ | CH₃ | 100(500) | |
| 36 | CONH₂ | CH₃ | 93(500) | HCl salt of (35) |
| 37(18) | CONHCH₃ | CH₃ | 100(500) | |
| 38(22) | CONH—n-C₄H₉ | CH₃ | 98(500) | |
| 39(23) | CONH—tert C₄H₉ | CH₃ | 99(1000) | |
| 40(51) | CONH—i-C₄H₉ | CH₃ | 97(500) | |
| 41(26) | CONHC(CH₃)₂CH₂C(CH₃)₃ | CH₃ | 60(1000) | |
| 42(19) | CONHC₂H₅ | CH₃ | 100(500) | |
| 43(20) | CONH(CH₂)₂CH₃ | CH₃ | 93(1000) | |
| 44(21) | CONHCH(CH₃)₂ | CH₃ | 100(500) | |
| 45(24) | CONH(CH₂)₅CH₃ | CH₃ | 80(2000) | |
| 46 | CONH(CH₂)₅CH₃ | CH₃ | 97(2000) | HCl salt of (45) |
| 47(25) | CONH(CH₂)₇CH₃ | CH₃ | 70(1000) | |
| 48(37) | CONH(CH₂)₂OH | CH₃ | 100(500) | |
| 49(63) | CONH(CH₂)₃OCH₃ | CH₃ | 100(1000) | |
| 50(27) | CONH—⟨S⟩ | CH₃ | 86(500) | |
| 51(29) | CONH—⌬ | CH₃ | 89(1000) | |
| 52 | 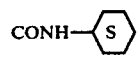 | CH₃ | 20(2000) | |
| 53 | 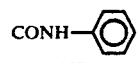 | 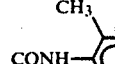 | 30(2000) | HCl salt |

TABLE C-continued

Basic structure:

$$\text{pyridine ring with } R^2, R^3, R^4, R^5 \text{ substituents, connected to } C(=N-CR^1=CR-)S \text{ thiazoline}$$

| No. | Substituent | R⁵ | Activity | Notes |
|---|---|---|---|---|
| 54(28) | CONHCH₂—C₆H₅ | CH₃ | 60(1000) | |
| 55(53) | CONH—(2-pyridyl) | CH₃ | 70(1000) | |
| 56(54) | CONH(CH₂)₃N(CH₃)₂ | CH₃ | 95(500) | |
| 57(30) | CON(CH₃)₂ | CH₃ | 100(500) | |
| 58(31) | CON(C₂H₅)₂ | CH₃ | 100(500) | |
| 59 | CON(C₂H₅)₂ | CH₃ | 100(500) | SO₄ salt of (58) |
| 60(32) | CON(i-C₃H₇)₂ | CH₃ | 80(500) | |
| 61(33) | CON(i-C₄H₉)₂ | CH₃ | 45(1000) | |
| 62(34) | CON(pyrrolidine) | CH₃ | 100(500) | |
| 63(35) | CON(piperidine) | CH₃ | 85(500) | |
| 64(36) | CON(morpholine) | CH₃ | 100(500) | |
| 65(59) | CON(2,6-dimethylmorpholine) | CH₃ | 95(1000) | |
| 66(55) | CON(CH₂CH=CH₂)₂ | CH₃ | 90(1000) | |
| 67(56) | CON(CH₃)—C₆H₅ | CH₃ | 94(1000) | |
| 68(57) | CON(C₂H₅)—C₆H₅ | CH₃ | 90(1000) | |
| 69(58) | CON(CH₂CH₂OH)(CH₃) | CH₃ | 80(1000) | |
| 70(62) | COOCH₃ | CH₂COOCH₃ | 80(1000) | |
| 71(71) | H | COOH | 85(2000) | |
| 72 | H | COOC₂H₅ | 40(2000) | |
| 73(70) | H | COOC₂H₅ | 60(2000) | HBr salt of (72) |
| 74 | H | COOCH₂C≡CH | 70(2000) | |
| 75(48) | H | CH₂COOH | 70(1000) | |
| 76(47) | H | CH₂COOC₂H₅ | 100(500) | |
| 77 | H | CH₂COOC₂H₅ | 100(1000) | HCl salt of (76) |
| 78(46) | H | CH₂COOCH₃ | 100(1000) | |
| 79(42) | H | CONH₂ | 90(500) | |
| 80(43) | H | CONHCH₃ | 60(2000) | |
| 81(44) | H | CON(C₂H₅)₂ | 75(1000) | |
| 82(45) | H | CON—(tetrahydropyran-4-yl) | 80(2000) | |
| 83 | H | CH₂CONH—C₆H₅ | 50(2000) | |
| 84 | H | CH₂CONH—C₆H₅ | 60(2000) | HBR salt of (83) |
| 85(50) | COOC₂H₅ | CH₃ | 95(1000) | R²=CH₃ |
| 86(49) | COOC₂H₅ | CH₃ | 90(500) | R³=CH₃ |

TABLE C-continued

Basic structure:

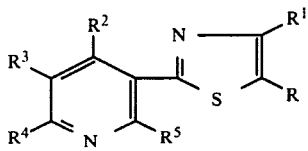

| | | | |
|---|---|---|---|
| 87 | 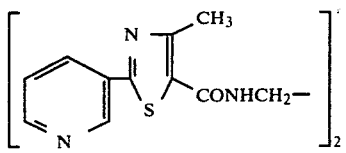 | | 90(2000) |
| 88 | 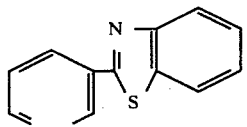 | | 86(500) |
| 89(74) | NO₂ | CH₂CH₃ | 20(1000) |
| 90(75) | 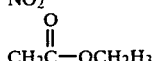 | CH₃ | 80(1000) |
| 91(76) | 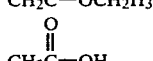 | CH₃ | 90(1000) |
| 92(77) | 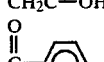 | CH₃ | 50(1000) |
| 93(78) | 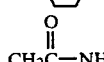 | CH₃ | 30(1000) |
| 94 | NO₂ | CH₂CH₃ | 90(1000) |
| 95(79) | 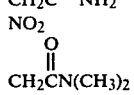 | CH₃ | 98(1000) |

Comparison Data

| | | |
|---|---|---|
| 96 | 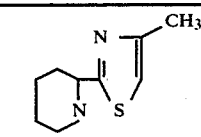 (2-pyridyl, not 3-pyridyl) | 0(2000) |
| 97 | 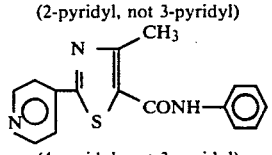 (4-pyridyl, not 3-pyridyl) | 0(2000) |
| 98 | 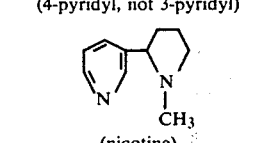 (nicotine) | 95(500) |

Numbers in parenthesis beside the compound number are taken from Table B.

EXAMPLE VII

A series of tests were made to show that the compounds of this invention protect the parts of a plant above ground when the compounds are applied to the soil in which the plant had its roots.

Seedling barley plants one to two weeks old were grown in cups containing a potting soil mixture. The weight of the soil in each cup was approximately 400 grams. The chemicals to be tested were dissolved or suspended in water at concentrations of 600 ppm and of 150 ppm. 26 ml aliquots of each concentration were applied to two pots each, giving a final dilution in the soil of approximately 40 ppm and 10 ppm respectively. The barley seedlings were infested with Corn Leaf Aphids, *Rhopalosiphum maidis*. After six days in the greenhouse, the population of aphids in the treated pots was compared to that of the untreated controls and the percent control recorded as shown in Table D.

TABLE D

| | % Control by Soil Drench | |
|---|---|---|
| Chemical | 40 PPM | 10 PPM |
| 4-methyl-2-(3-pyridyl)thiazole | 100 | 95 |
| 4-methyl-2-(3-pyridyl)thiazole hydrochloride | 100 | 100 |
| 4,5-dimethyl-2-(3-pyridyl) | | |

TABLE D-continued

| Chemical | % Control by Soil Drench | |
|---|---|---|
| | 40 PPM | 10 PPM |
| thiazole | 100 | 95 |
| 4-methyl-2-(3-pyridyl)-5-thiazolecarboxylic acid | 100 | 0 |
| Ethyl 4-methyl-2-(3-pyridyl)-5-thiazolecarboxylate | 100 | 100 |
| 5-acetyl-4-methyl-2-(3-pyridyl)thiazole | 85 | 40 |
| 4-methyl-2-(3-pyridyl)-5-thiazolecarboxamide | 100 | 90 |
| 4-methyl-2-(3-pyridyl)-5-thiazolecarboxanilide | 95 | 15 |
| 4-ethyl-2-(3-pyridyl)thiazole | 90 | 40 |
| 4-ethyl-2-(3-pyridyl)thiazole hydrochloride | 100 | 80 |
| Nicotine | 0 | 0 |

In this test, a systemic effect was demonstrated. The plants apparently absorbed the compounds through their roots and transmitted them to the aphid-infested portions where the compounds killed the insects.

EXAMPLE VIII

This example demonstrates the selective effect of one of the preferred compounds in controlling insects, namely ethyl 4-methyl-2-(3-pyridyl)-5-thiazolecarboxylate (A).

The compound was prepared for use by adding 15 grams to 37 milliliters (ml) of super high flash naphtha and 3 ml of Emulfor 719, an emulsifier, and then diluting with water to make up 7½ liters for a concentration of 2000 parts per million (ppm) of active ingredient. Similarly, dilutions were made to produce concentrations of 1000 ppm and 500 ppm.

The emulsions were applied as sprays to 10-foot apple trees that had been heavily infested with Green Apple aphids, *Aphis pomi*. The foliage of the trees was sprayed until thoroughly drenched.

Three days after spraying, leaves on ten shoots per tree were examined for aphids, and the number of aphids present was compared to the number on untreated trees, and to trees sprayed with phosphamidon (B), a commercially available broad spectrum insecticide. Results were:

TABLE E

| Compound | Rate, ppm | No. Trees | % Control Aphids | Syrphid Larvae on 10 shoots* |
|---|---|---|---|---|
| A | 2000 | 5 | 96 | 1.2 |
| A | 100 | 3 | 88 | 2.3 |
| A | 500 | 4 | 85 | 1.25 |
| B | 300 | 5 | 99 | 0 |
| None | — | 4 | 0 | 0.25 |

*Average after spraying.

The results showed effective aphid control with both A and B. But B killed the beneficial insects (syrphid larvae); its activity was not selective. A selectively killed only harmful insects.

EXAMPLE IX

Many of the compounds of this invention are useful for killing mosquitos.

Compounds were prepared for this use by dissolving 30 milligrams (mg) of each in 10 ml of acetone. Dilutions were made with water to the desired concentration. Two 25 ml aliquots were placed in test tubes to which were added 10 to 25 mosquito larvae. The larvae were fourth instar larvae of the yellow fever mosquito, *Aedes aegypti*.

The tubes were held at 70° Fahrenheit (F.) in darkness for 72 hours. At the end of this period, the live and dead larvae were counted, and the percent control was calculated. The results:

TABLE F

| Compound | % Control Mosquito Larvae (Dosage 10 ppm) |
|---|---|
| 4'-Chloro-4-methyl-2-(3-pyridyl)-5-thiazolecarboxanilide | 80 |
| 2-(3-pyridyl)-4,5-thiazoledicarboxy-o-toluidide | 90 |

What is claimed:

1. A compound having the general formula $$\text{[structure: pyridyl-thiazole with } CH_3 \text{ and } C(=O)-NR_8R_9 \text{ substituents]}$$

wherein $R_8$ and $R_9$ are independently selected from the group consisting of (1) hydrogen; (2) alkyl, alkenyl, hydroxyalkyl, alkoxyalkyl, aminoalkyl, alkylaminoalkyl containing up to 8 carbon atoms; (3) $C_5$ to $C_8$ cycloalkyl; and (4) $C_6$–$C_{10}$ aryl, haloaryl, aralkyl, alkaryl.

2. The compound of claim 1 wherein $R_8$ and $R_9$ are both H.

3. The compound of claim 1 wherein $R_8$ is H and $R_9$ is methyl, ethyl, propyl, isopropyl, butyl, isobutyl, sec-butyl, tert-butyl, hexyl, octyl, tert-octyl, cyclohexyl, benzyl, hydroxyethyl, aminoethyl, dimethyl aminopropyl, methoxypropyl, phenyl or p-chlorophenyl.

4. The compound of claim 1 wherein $R_8$ and $R_9$ are the same and are methyl, ethyl, isopropyl, allyl or isobutyl.

5. The compound of claim 1 wherein $R_8$ is methyl and $R_9$ is hydrooxyethyl.

6. The compound of claim 1 wherein $R_8$ is ethyl and $R_9$ is phenyl.

7. The compound of claim 1 wherein said compound is N,4-dimethyl-2-(3-pyridyl)-5-thiazolecarboxamide.

8. The compound of claim 1 wherein said compound is N-ethyl-4-methyl-2-(3-pyridyl)-5-thiazolecarboxamide.

9. The compound of claim 1 wherein said compound is N,N,4-trimethyl-2-(3-pyridyl)-5-thiazolecarboxamide.

10. The compound of claim 1 wherein said compound is N,N-diethyl-4-methyl-2-(3-pyridyl)-5-thiazolecarboxamide.

* * * * *